United States Patent [19]

Maurer et al.

[11] Patent Number: 5,010,895
[45] Date of Patent: Apr. 30, 1991

[54] EXPANDABLE VAGINAL ELECTRODE

[75] Inventors: Donald D. Maurer; Stacy D. Mattson, both of Anoka, Minn.

[73] Assignee: Empi, Inc., St. Paul, Minn.

[21] Appl. No.: 389,175

[22] Filed: Aug. 3, 1989

[51] Int. Cl.⁵ .............................................. A61N 1/05
[52] U.S. Cl. ................................................. 128/788
[58] Field of Search ................. 128/642, 783, 784, 788

[56] References Cited

U.S. PATENT DOCUMENTS

| | | | |
|---|---|---|---|
| 659,409 | 10/1900 | Mosher | 369/157 |
| 1,622,244 | 3/1927 | Beckley | 128/798 |
| 2,110,392 | 3/1938 | Dorr | 128/413 |
| 3,654,933 | 4/1972 | Hagfors | 128/418 |
| 3,926,178 | 12/1975 | Feldzamen | 128/2 |
| 4,094,309 | 6/1978 | Grzenia | 128/2.06 |
| 4,106,511 | 8/1978 | Erlandsson | 128/788 |
| 4,296,760 | 10/1981 | Carlsson et al. | 128/788 |
| 4,300,575 | 11/1981 | Wilson | 128/798 |
| 4,509,535 | 4/1985 | Bryan | 128/798 |
| 4,515,167 | 5/1985 | Hochman | 128/736 |
| 4,542,753 | 9/1985 | Brenman et al. | 128/788 |
| 4,602,624 | 7/1986 | Naples et al. | 128/784 |
| 4,722,353 | 2/1988 | Sluetz | 128/785 |
| 4,762,135 | 8/1988 | van der Puije et al. | 128/784 |
| 4,781,196 | 11/1988 | Killion | 128/642 |
| 4,785,828 | 11/1988 | Maurer | 128/788 |

FOREIGN PATENT DOCUMENTS 2502620 7/1975 Fed. Rep. of Germany .

Primary Examiner—Kyle L. Howell
Assistant Examiner—Kevin Pontius
Attorney, Agent, or Firm—Kinney & Lange

[57] ABSTRACT

A vaginal electrode adapted to be inserted into a woman's vagina and used as part of a stimulation system to stimulate and constrict muscles surrounding the vagina to prevent the flow of urine through the urethra. The electrode includes a nonconductive sheet of material formed into a diametrically compressible spiral tending to unwind. An exterior surface of the sheet contacts the interior vaginal wall after the electrode is inserted into a vagina. Conductive electrode elements circumferentially oriented on the exterior surface of the sheet are thereby forced into electrical contact with the vaginal wall. Leads couple electrical stimulation signals to the electrode elements.

27 Claims, 2 Drawing Sheets

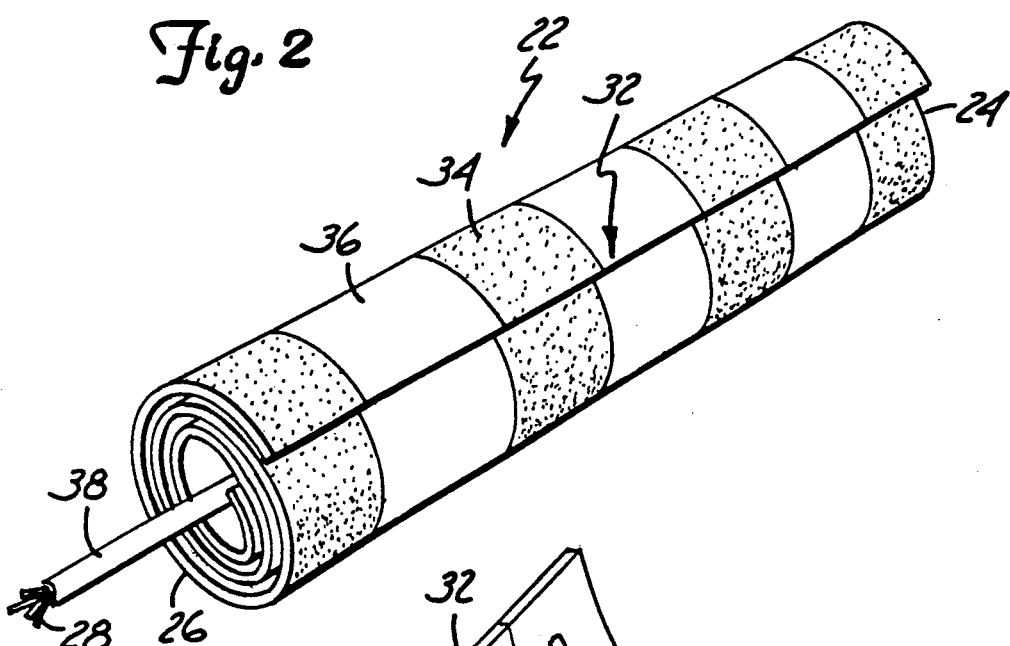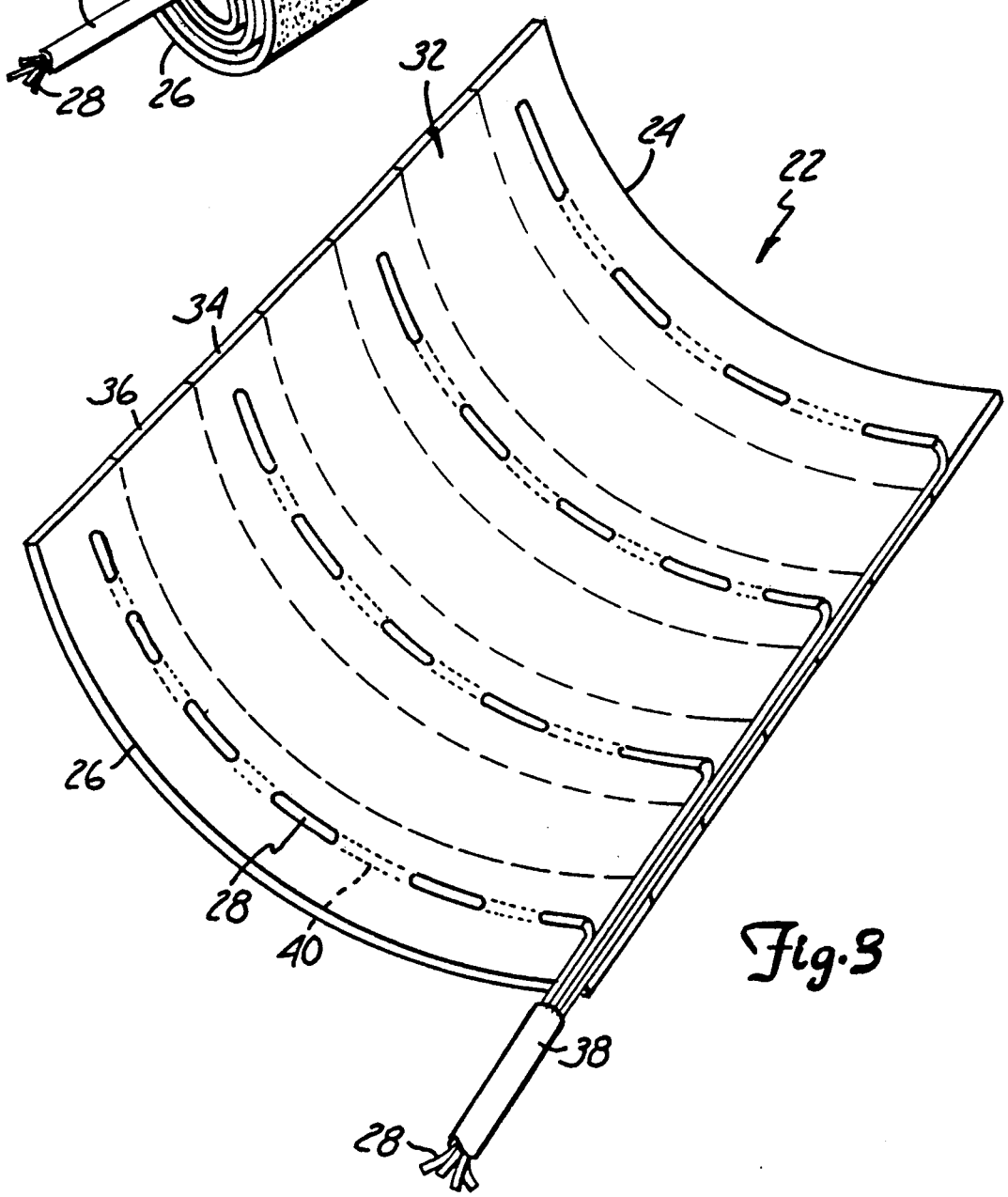

– 5,010,895 –

EXPANDABLE VAGINAL ELECTRODE

BACKGROUND OF THE INVENTION

1. Field of the Invention

The present invention relates generally to electrical neuromuscular stimulators. In particular, the present invention is vaginal electrode for use as part of a neuromuscular stimulation system for controlling urinary incontinence in women.

2. Description of the Prior Art

Neuromuscular electrical stimulation, whereby motor nerve fibers are stimulated by means of transcutaneously applied pulses of electrical current to cause contraction of muscles the fibers innervate, is widely used to assist persons afflicted with motor dysfunctions in performing muscle contraction maneuvers. This technique is also used to re-educate patients in the proper use of the dysfunctional muscles.

For cases in which female urinary incontinence is caused by the patient's inability to properly contract the external sphincter of the urethra, it has been shown that the use of a neuromuscular stimulation system can effectively prevent the unwanted flow of urine. Furthermore, use of such a stimulation system can re-educate the patient to voluntarily or automatically impede the flow of urine. After a period of time during which the stimulation is used, a woman may be able to maintain herself dry without continued use of the device.

Known stimulation systems for controlling urinary incontinence usually utilize plug-type electrode carriers which are insertable into a vagina and made in a broad variety of sizes in an attempt to accommodate an individual patient's anatomy. Even with the broad variety of sizes of electrode carriers available, finding a size to make a proper fit within a vagina is not ensured. In addition, even when a proper fit is made, changes in the vagina size due to hormone level changes or changes in body position can result in the electrode/carrier no longer properly fitting the vagina. As a consequence of the change in vagina size, the electrode/carrier structure tends to slide out of the vagina, with the surface of the electrode loosing direct electrical contact with the vaginal wall.

Clearly, there is a continuing need for improved vaginal electrodes for use with incontinence stimulation systems. In addition to being effective when used as part of a stimulation system, the electrode must be convenient to use. The device must therefore be capable of accommodating a range of vagina sizes. The device must be easy to insert. The device must also maintain contact between the electrode surfaces and the vaginal walls during changes in body position and changes in hormone levels.

SUMMARY OF THE INVENTION

The present invention is a vaginal electrode insertable into a woman's vagina as part of a stimulation system for stimulating and constricting muscles adjacent the vagina to prevent the flow of urine through the urethra. The electrode includes an elongated resilient member with an exterior surface on which a plurality of conductive electrode elements reside, and leads for coupling electrical stimulation signals to the electrode elements. The elongated resilient member is capable of transverse compression permitting its insertion into a vagina. The elongated resilient member is also capable of transverse expansion, causing its exterior surface and electrode elements to contact the vagina after insertion within the vagina.

In one embodiment, the electrode includes a diametrically compressible, spiral rolled sheet of material, with an exterior surface contacting the vaginal wall after insertion into the vagina. Circumferentially oriented electrode elements are positioned on the exterior surface of the sheet. Leads are woven into the sheet and couple electrical signals to the electrode elements.

The vaginal electrode of the present invention is convenient and easy to use. A single vaginal electrode can accommodate a full range of individual patient anatomies. This characteristic alleviates the inconvenience of having to choose the proper size electrode. Furthermore, once the vaginal electrode is inserted into the vagina, changes due to such factors as hormone levels or body position which can cause changes in the vagina size, are compensated for by the compressible/expandable nature of the electrode. Thus, contact between the electrode elements and the vaginal wall is maintained as well as the retention of the electrode within the vagina.

BRIEF DESCRIPTION OF THE INVENTION

FIG. 2 is a perspective view of the electrode in its rolled spiral state.

FIG. 3 is a perspective view of the electrode in an unrolled, expanded state.

DETAILED DESCRIPTION OF THE PREFERRED EMBODIMENTS

Figure 1:
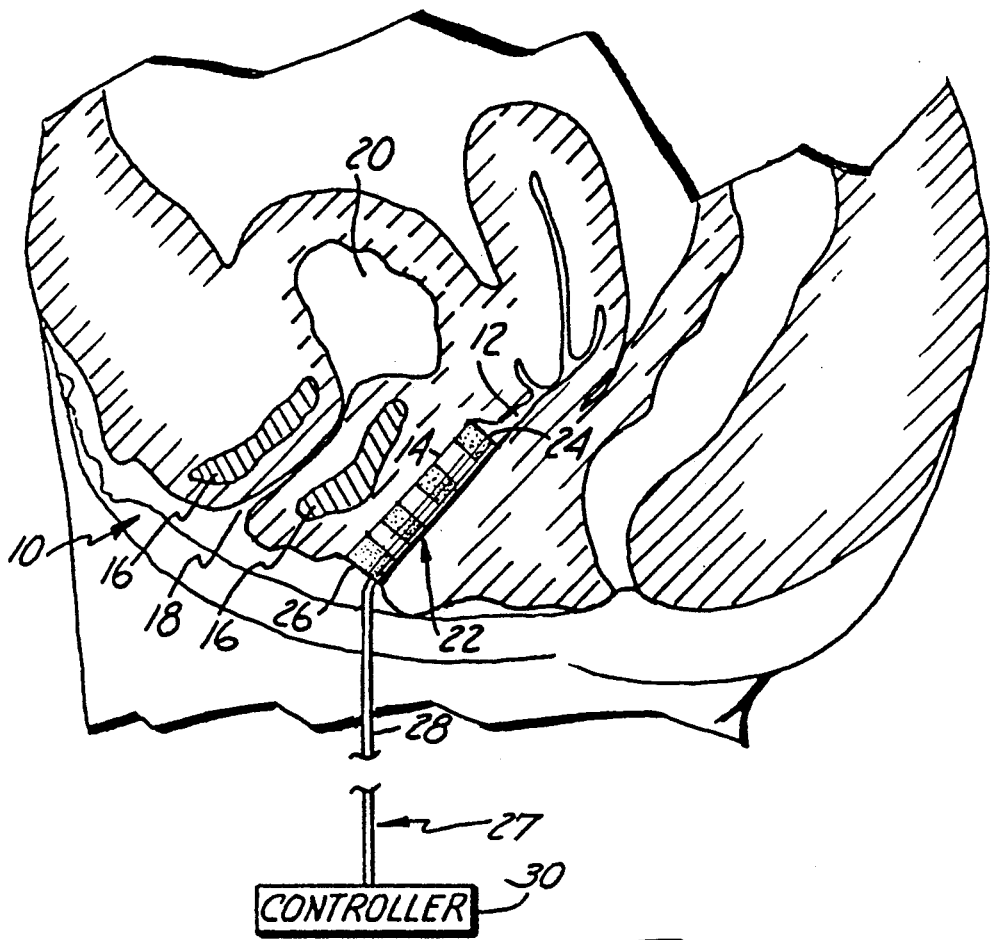
FIG. 1 is a cross-sectional view showing an electrode in accordance with the present invention operatively disposed in the vagina of a user.

A vaginal electrode 22 in accordance with the present invention is shown operatively disposed within a woman's pelvic region in FIG. 1. Pelvic region 10 includes a vagina 12 having vaginal walls 14, a urethra 18, and sphincter muscles 16 surrounding the urethra. Electrical stimulation of pelvic region 10 by vaginal electrode 22 causes contraction of sphincter muscles 16, thereby constricting urethra 18 and preventing the unwanted flow of urine from bladder 20.

Vaginal electrode 22 has a distal end 24 positioned within vagina 12 and a proximal end 26 positioned adjacent an introitus of vagina 12. Vaginal electrode 22 is part of stimulation system 27, which also includes conductive leads 28 and controller 30. Leads 28 extend out of proximal end 26 and couple electrical signals from controller 30 to vaginal electrode 22. Controller 30 is selectively operable to send a train of pulsed electrical signals of varying intensity (e.g. amplitude and pulse width) and frequency through leads 28 to vaginal electrode 22.

Vaginal electrode 22, as illustrated in FIGS. 2 and 3, is an elongated member that is resilient and capable of both transverse compression and transverse expansion. Vaginal electrode 22 includes a sheet of material 32 which is shown in FIG. 2 in a diametrically compressed, rolled spiral state. When sheet 32 is in its compressed spiral state, electrode 22 can be inserted and positioned within vagina 12. Sheet 32 also retains an expanded, rolled spiral configuration when sheet 32 is not diametrically compressed. The tendency of sheet 32 to unwind from its compressed spiral state to its expanded spiral state provides an outwardly oriented transverse or diametric pressure so that electrode 22 is retained within vagina 12. FIG. 3 shows sheet 32 in a forced, expanded or unrolled state illustrating its interior surface and sheet-like geometrical qualities. Sheet 32 can be formed from polymer materials, polymer-covered metals or other nonconductive shape-memory materials.

Electrode elements 34 are positioned parallel to one another and mounted in a circumferentially oriented fashion upon the exterior surface of rolled sheet 32. Electrode elements 34 are comprised of a conductive material such as conductive polymer or carbon-loaded silicone rubber.

Nonconductive elements 36 separate and insulate conductive electrode elements 34 from one another. Non-conductive elements 36 are positioned parallel to one another and mounted in a circumferentially oriented fashion upon the exterior surface of rolled sheet 32. Nonconductive elements 36 are made of a nonconductive material such as nonconductive silicone rubber.

Lead housing 38 extends from proximal end 26 of rolled sheet 32 and protects leads 28. Housing 38 also provides structural support for leads 28 to facilitate handling of vaginal electrode 22 during insertion, positioning, and removal. In the embodiment shown in FIG. 3, leads 28 are woven into sheet 32 parallel to one another. Contact portions 40 of leads 28 (shown in phantom in FIG. 3) are exposed on the exterior surface of sheet 32, contacting electrode elements 34 to provide the coupling of electrical signals. Electrode elements 34 and nonconductive elements 36 can be layers applied to sheet 32 after leads 28 are woven in the sheet.

In operation, the use of vaginal electrode 22 as part of stimulation system 27, begins with the insertion of vaginal electrode 22 into vagina 12. Prior to insertion, vaginal electrode 22 must first be transversely compressed into a spiral by rolling and circumferentially applying pressure to rolled sheet 32 so that the diameter thereof permits insertion within the introitus of vagina 12. Next, while holding vaginal electrode 22 by hand to maintain the compressed spiral state, the distal end 24 of vaginal electrode 22 is inserted through the introitus into vagina 12 until proximal end 26 is adjacent the introitus.

Once vaginal electrode 22 is inserted and positioned within vagina 12, rolled sheet 32 unwinds and transversely expands (i.e., has spring-like shape memory) until its diameter increases to such an extent that electrode elements 34 establish contact with vaginal walls 14. Vaginal electrode 22 is retained in vagina 12 with electrode elements 34 forced into electrical contact with vaginal walls 14 by the tendency of rolled sheet 32 to unwind. This transverse pressure is consistently maintained so hormone level changes or changes in body position do not alter retention of electrode 22 within vagina 12.

After vaginal electrode 22 is firmly seated within vagina 12, controller 30 (which is typically clipped to the clothing of the user) is manipulated by an operator to provide stimulating signals to electrode elements 34. The active electrode elements 34 in contact with vaginal walls 14 transcutaneously transmit the stimulation signals to pelvic region 10 so as to cause contraction of muscles 16, thereby constricting urethra 18. The illustrated embodiment of electrode 22 includes four electrode elements 34. Stimulation signals can be applied through one or more pairs of electrodes 22 to most effectively recruit muscles 16. The use of vaginal electrode 22 as part of stimulation system 27 provides an effective tool in controlling female urinary incontinence.

Although the present invention has been described with reference to preferred embodiments, workers skilled in the art will recognize that changes may be made in form and detail without departing from the spirit and scope of the invention.

What is claimed is:
1. A vaginal electrode, including:
   a sheet of material having a first surface and windable into a spiral, the sheet of material tending to unwind after insertion into a woman's vagina to force the first surface against the vaginal wall;
   a plurality of electrically isolated conductive electrode elements on the first surface of the sheet of material so as to contact the vaginal wall after insertion; and
   leads for coupling electrical signals to the electrode elements.
2. The electrode of claim 1 wherein the wound spiral sheet of material forms several overlapping layers.
3. The electrode of claim 1 wherein the sheet of material includes a polymer sheet.
4. The electrode of claim 1 wherein the sheet of material includes a polymer-covered, thin metal sheet.
5. The electrode of claim 1 wherein the sheet of material includes a nonconductive sheet of shape memory material.
6. The electrode of claim 1 wherein the electrode elements include conductive polymer elements.
7. The electrode of claim 6 wherein the electrode elements include carbon-loaded silicone rubber.
8. The electrode of claim 7 and further including nonconductive silicone rubber between the electrode elements on the first surface of the sheet.
9. The electrode of claim 1 wherein:
   the leads include conductors woven into the sheet of material and having contact portions which extend from the first surface; and
   the electrode elements include conductive elements on the first surface of the sheet and in electrical contact with the contact portions of the leads.
10. The electrode of claim 9 wherein the electrode elements include conductive polymer elements.
11. The electrode of claim 10 wherein the electrode elements include carbon-loaded silicone rubber.
12. The electrode of claim 11 and further including nonconductive silicone rubber on the first surface of the sheet between the electrode elements.
13. A vaginal electrode, including:
   a nonconductive sheet of material formed into a diametrically compressible spiral constructed to unwind, with a first surface contacting a vaginal wall after insertion into the vagina;
   conductive leads woven into the sheet having contact portions exposed on the first surface of the sheet;
   conductive electrode elements extending along the first surface of the sheet and in electrical contact with the contact portions so as to contact the vaginal wall after insertion; and
   nonconductive strips extending along the first surface of the sheet between the electrode elements.
14. The electrode of claim 13 wherein the wound nonconductive sheet of material forms several overlapping layers.
15. The electrode of claim 13 wherein the sheet of material includes a polymer sheet.

16. The electrode of claim 13 wherein the sheet of material includes a polymer-covered, thin metal sheet.

17. The electrode of claim 13 wherein the sheet of material includes a nonconductive sheet of shape memory material.

18. The electrode of claim 13 wherein the electrode elements include conductive polymer elements.

19. The electrode of claim 18 wherein the electrode elements include carbon loaded silicon rubber.

20. The electrode of claim 13 wherein the strips include nonconductive silicon rubber strips.

21. The electrode of claim 13 wherein the leads are oriented perpendicular to the longitudinal axis of the spiral.

22. The electrode of claim 13 wherein the electrode elements are oriented perpendicular to the longitudinal axis of the spiral.

23. A vaginal electrode, including:
   a nonconductive sheet of material wound to form a diametrically compressible spiral having several layers and constructed to unwind, with a first surface contacting a vaginal wall after insertion into the vagina;
   a plurality of electrically isolated conductive electrode elements positioned on the first surface of the nonconductive sheet to contact the vaginal wall after insertion; and
   leads for coupling electrical signals to the electrode elements.

24. The electrode of claim 23 wherein the nonconductive sheet of material includes a sheet of shape memory material.

25. The electrode of claim 23 wherein:
   the leads include conductors woven into the sheet of material and having contact portions which extend from the first surface; and
   the electrode elements include conductive elements on the first surface of the sheet and in electrical contact with the contact portions of the leads.

26. The electrode of claim 25 wherein the electrode elements include conductive polymer elements.

27. The electrode of claim 26 wherein the electrode elements include carbon-loaded silicone rubber.

* * * * *

UNITED STATES PATENT AND TRADEMARK OFFICE
CERTIFICATE OF CORRECTION

PATENT NO. : 5,010,895
DATED : April 30, 1991
INVENTOR(S) : Donald D. Maurer et al.

It is certified that error appears in the above-identified patent and that said Letters Patent is hereby corrected as shown below:

Col. 4, line 11, delete "tending", insert --constructed--.

Signed and Sealed this

Seventeenth Day of November, 1992

Attest:

DOUGLAS B. COMER

Attesting Officer  Acting Commissioner of Patents and Trademarks